(12) United States Patent
Masini

(10) Patent No.: US 8,721,730 B2
(45) Date of Patent: May 13, 2014

(54) MULTIPLE-CAM, POSTERIOR-STABILIZED KNEE PROSTHESIS

(75) Inventor: Michael A. Masini, Ann Arbor, MI (US)

(73) Assignee: MedIdia, LLC, Ann Arbor, MI (US)

( * ) Notice: Subject to any disclaimer, the term of this patent is extended or adjusted under 35 U.S.C. 154(b) by 268 days.

(21) Appl. No.: 12/337,280

(22) Filed: Dec. 17, 2008

(65) Prior Publication Data

US 2009/0164022 A1 Jun. 25, 2009

Related U.S. Application Data

(60) Continuation of application No. 10/430,548, filed on May 6, 2003, now Pat. No. 8,273,132, which is a division of application No. 09/724,100, filed on Nov. 28, 2000, now Pat. No. 6,558,426.

(51) Int. Cl.
*A61F 2/38* (2006.01)

(52) U.S. Cl.
USPC ..................... 623/20.27; 623/13.12

(58) Field of Classification Search
USPC ................. 623/13.12, 20.21–20.28
See application file for complete search history.

(56) References Cited

U.S. PATENT DOCUMENTS

| | | | |
|---|---|---|---|
| 4,213,209 A | 7/1980 | Insall et al. | |
| 4,249,270 A | * 2/1981 | Bahler et al. | 623/20.27 |
| 4,298,992 A | * 11/1981 | Burstein et al. | 623/20.27 |
| 4,650,490 A | 3/1987 | Figgie, III | |
| 4,888,021 A | 12/1989 | Forte et al. | |
| 4,892,547 A | 1/1990 | Brown | |
| 4,936,847 A | 6/1990 | Manginelli | |
| 4,936,853 A | 6/1990 | Fabian et al. | |
| 4,959,071 A | 9/1990 | Brown et al. | |
| 5,007,932 A | 4/1991 | Bekki et al. | |
| 5,007,933 A | 4/1991 | Sidebotham et al. | |
| 5,011,496 A | 4/1991 | Forte et al. | |
| 5,133,759 A | 7/1992 | Turner | |
| 5,147,405 A | * 9/1992 | Van Zile et al. | 623/20.27 |
| 5,147,406 A | 9/1992 | Houston et al. | |
| 5,152,797 A | 10/1992 | Luckman et al. | |
| 5,236,461 A | 8/1993 | Forte | |

(Continued)

OTHER PUBLICATIONS

S.I. Bin, T. S. Nam, "Early results of high-flex total knee arthroplasty: comparison study at 1 year after surgery," Knee Surg. Sports Traumatol Arthrosc (2007) 15:350-355, Oct. 2006.

(Continued)

*Primary Examiner* — Thomas J Sweet
*Assistant Examiner* — Christopher D Prone
(74) *Attorney, Agent, or Firm* — Gifford, Krass, Sprinkle, Anderson & Citkowski, P.C.

(57) ABSTRACT

A distal femoral knee-replacement component provides additional points of cam action by either distinct bars or interconnected structural elements such as cam extensions to prevent early translation of the knee or dislocation of the femoral component over the tibial post which can occur in cruciate-substituting designs.

20 Claims, 5 Drawing Sheets

(56) References Cited

U.S. PATENT DOCUMENTS

| | | |
|---|---|---|
| 5,330,534 A | 7/1994 | Herrington et al. |
| 5,358,527 A | 10/1994 | Forte |
| 5,370,699 A | 12/1994 | Hood et al. |
| 5,480,445 A | 1/1996 | Burkinshaw |
| 5,549,686 A | 8/1996 | Johnson et al. |
| 5,549,687 A | 8/1996 | Coates et al. |
| D374,078 S | 9/1996 | Johnson et al. |
| 5,554,158 A | 9/1996 | Vinciguerra et al. |
| 5,639,279 A | 6/1997 | Burkinshaw et al. |
| 5,658,342 A | 8/1997 | Draganich et al. |
| 5,702,458 A | 12/1997 | Burstein et al. |
| 5,800,552 A | 9/1998 | Forte |
| 5,824,100 A | 10/1998 | Kester et al. |
| 5,879,392 A | 3/1999 | McMinn et al. |
| 5,997,577 A | 12/1999 | Herrington et al. |
| 6,325,828 B1 | 12/2001 | Dennis et al. |

OTHER PUBLICATIONS

R. E. Jones, "High-Flexion Rotating-Platform Knees: Rationale, Design and Patient Selection," Orthopedics, vol. 29, No. 9, Sep. 2006.

G. Li, E. Most, P. Sultan, S. Schule, S. Zayontz, S. Park, H. Rubash, "Knee Kinematics with a High-Flexion Posterior Stabilized Total Knee Prosthesis: An In Vitro Robotic Experimental Investigation," Journal of Bone and Joint Surgery, vol. 86, No. 8, Aug. 2004.

J. Argenson, R. Komistek, M. Mahfouz, S. Walker, J. Aubaniac, D. Dennis, "A High Flexion Total Knee Arthroplasty Design Replicates Healthy Knee Motion," Clinical Orthopaedics and Related Research, No. 428, pp. 174-179, (2004).

PubMed Abstracts, downloaded Jul. 18, 2007 (www.pubmed.gov).

* cited by examiner

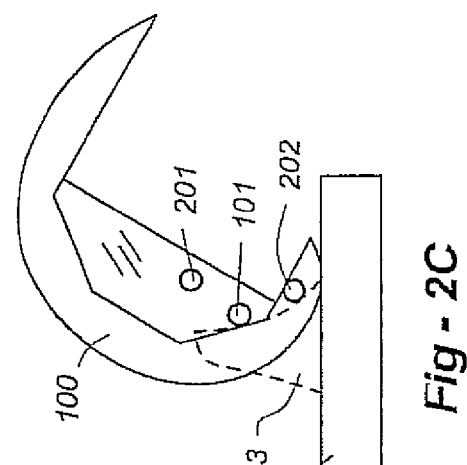
*Fig - 2A*
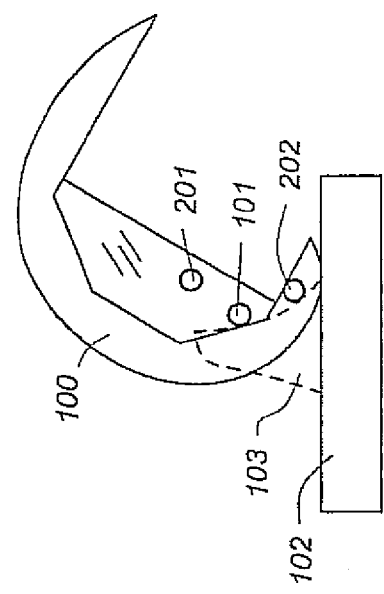
*Fig - 2B*
*Fig - 2C*
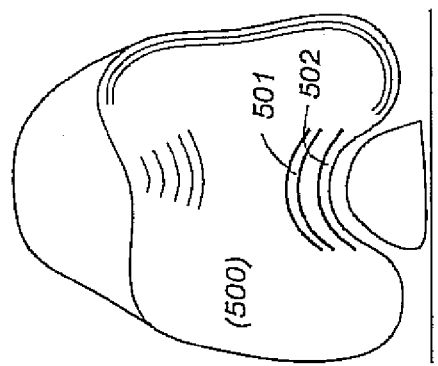
*Fig - 4*
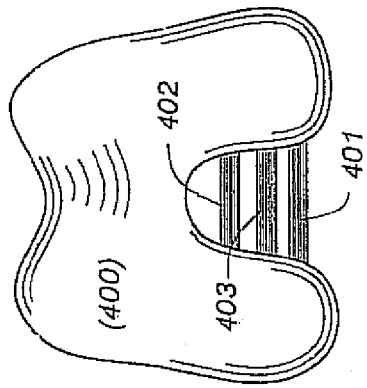
*Fig - 5*
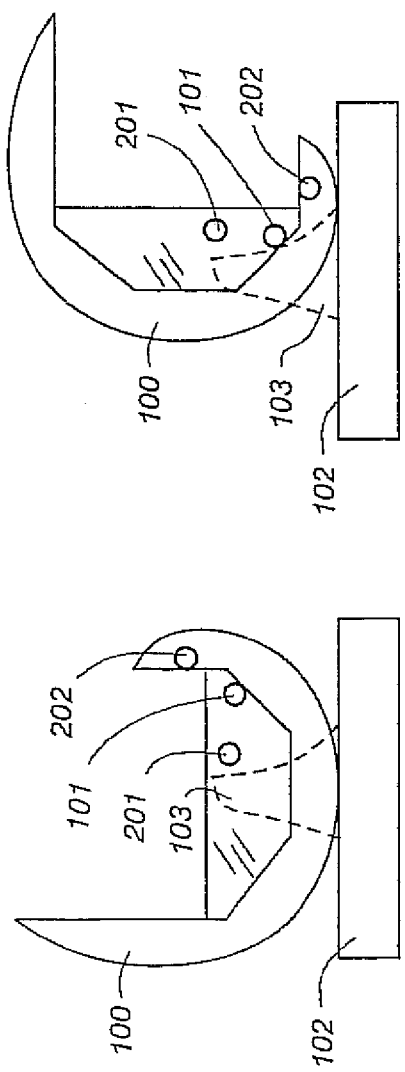
*Fig - 3*

MULTIPLE-CAM, POSTERIOR-STABILIZED KNEE PROSTHESIS

REFERENCE TO RELATED APPLICATIONS

This application is a continuation of U.S. patent application Ser. No. 10/430,548, filed May 6, 2003, now U.S. Pat. No. 8,273,132, which is a divisional of U.S. patent application Ser. No. 09/724,100, filed Nov. 28, 2000, now U.S. Pat. No. 6,558,426, the content of both of which are incorporated herein in their entirety by reference.

FIELD OF THE INVENTION

This invention relates generally to orthopedic surgery and, in particular, to a posterior stabilized knee prosthesis.

BACKGROUND OF THE INVENTION

In total knee-replacement (TKR) surgery, there are four broad classes of implants used for resurfacing of the distal femur. In one configuration, the posterior cruciate ligament is retained. In another design the ligament is sacrificed, relying on the articular geometry to provide stability. The third type of device is constrained, in the sense that an actual linkage is used between the femoral and tibial components. According to a fourth arrangement, the posterior cruciate is replaced with a cam on the femoral component and a post on the tibial component.

Many patents have been issued in relation to these design configurations, including the cam-and-post design configuration. Some of the earlier patents in this area include U.S. Pat. No. 4,213,209 to Insall et al; U.S. Pat. No. 4,298,992 to Burstein et al.

Other patents include U.S. Pat. No. 4,888,021 to Forte et al., which teaches a cam-and-post mechanism as well as a linking mechanism. Essentially, each component includes a varying surface and a cam member, so that both the tibial and the femoral component have separate and distinct cams that cooperate with a single tibial post.

U.S. Pat. No. 5,824,100 to Kester et al. discloses a cam/post type of arrangement with a unique type of cam and box enclosure. A portion of the box enclosure is intended to prevent hyperextension and posterior translation. As noted in particular in FIGS. 3 and 4 of the '100 patent, a large space exists between the cam 110 and the post 100 which permits a translation to occur prior to engagement of the cam left of post.

U.S. Pat. No. 5,997,577 to Herrington et al. provides a cam on the femur with a geometry meant to contact the post through a large range of motion. This design attempts to provide the function of multiple cams by providing an area that acts as a separate bearing surface. As such, the cam effectively moves through a range of motion while contacting the post. Depending on the articular geometry which differs than the geometry of the cam post mechanism, this could lead to a variety of problems as well as significantly constrained motion, either between the cam and the post or between the two articulating surfaces.

U.S. Pat. No. 5,658,342 to Draganich et al. describes a cam member with including a bearing surface at complimenting an articulating surface. As in other previous designs, this represents a complex cam geometry meant to capture the post in certain degrees of the range of motion.

U.S. Pat. No. 5,147,405 to Van Zyle et al. Discloses a femoral component with two distinct cam structures, one located at point 44, the other located at 46 in the drawings. The cam member 44 is meant to contact the anterior surface of the post 24 to prevent hyperextension, while cam surface 46 is a posterior located cam meant to have contact throughout the range of flexion. As noted in FIG. 6A of the '405 patent, there is a space between the cam and the post when the knee is in extension, necessitating anterior translation of the femur on the tibia prior to contacting the posterior cam.

Many other patents directed to knee-replacement surgery include cam-and-post mechanisms. But in all cases, either the full range of joint motion is precluded, or translation is allowed to occur which could lead to premature wear. FIG. 1 is a drawing which illustrates a typical prior-art cam-and-post mechanism. Item 102 is a tibial insert or tibial component having a post 103 protruding into a box-like recess of the femoral component 100. FIG. 1A shows the system in extension, whereas FIG. 1B shows the system in flexion. In FIG. 1A, a femoral component 100 includes a cam 101 which has not yet engaged with a post 103.

In FIG. 1B, following a considerable amount of flexion, the cam 101 finally engages with the post 103. Until engagement occurs, however, the component 100 may be permitted to slide relative to the tibial insert. The need remains, therefore, for an improved distal femoral prosthesis having multiple distinct cams contacting a post on its posterior surface to a provide more normal range of motion for cruciate substituting knee replacement.

SUMMARY OF THE INVENTION

The present invention resides in a distal femoral knee-replacement component configured for use in a cruciate-substituting situation involving a tibial component having a bearing surface and a superior post with a posterior aspect. As with existing configurations, the component is comprised of a body having a pair of medial and lateral condylar protrusions and an intercondylar region therebetween dimensioned to receive the tibial post. In contrast to prior-art devices, however, the inventive component provides additional points of cam action to facilitate a more normal range of knee motion.

In the preferred embodiment, the invention facilitates a more normal rollback while inhibiting initial translation which could lead to increased wear and sub-optimal patella femoral mechanics. To accomplish this goal, the inventive component includes a distinct point of cam action to prevent early translation at the initiation of flexion, and a distinct point of cam action to prevent a dislocation of the femoral component over the tibial post which is known to occur in cruciate-substituting designs. According to the invention, these points of cam action may be used separately or in combination.

In the preferred embodiment, the component includes three distinct points of cam action. The first is preferably located substantially where existing cams are found, namely, at a point spaced apart a slight distance posteriorly relative to the post in full extension. According to the invention, however, a second point of cam action is located immediately adjacent the posterior aspect of the superior post to minimize and, ideally, prevent anterior translation at the initiation of flexion. The third point of cam action is preferably located more posteriorly to allow enhanced flexion without a dislocation of the knee.

In terms of structure, the points of cam action may be implemented using any member or combination of elements operative to provide distinct stages of cooperation with the posterior aspect of the superior post. For example, transverse bars may be used which bridge, or partially bridge, the intercondylar space. The members or elements need not be straight across, but may instead be curved, with the post being curved to allows for a rotation, if so desired. The cam structures according to the invention may also be connected to one another forming points of contact as opposed to complete transverse elements such as distinct bars.

BRIEF DESCRIPTION OF THE FIGURES

FIG. 2A illustrates a preferred embodiment of the invention in extension;

FIG. 2B shows the system of FIG. 2A at 90 degrees flexion;

FIG. 2C illustrates the system of FIG. 2A in flexion at 120 degrees or more;

FIG. 3 shows an anterior view of a prior-art cruciate-substituting knee-replacement component;

FIG. 4 shows a knee prosthesis according to the invention having multiple cams as seen in a distal-to-proximal view;

FIG. 5 is a drawing which shows how cam-acting members according to the invention need not be straight across, but may be curved in conjunction with a curved post to facilitate rotation.

DETAILED DESCRIPTION OF THE INVENTION

FIGS. 2A through 2C illustrate one embodiment of the invention. FIG. 2A shows the configuration in extension, FIG. 2B shows the system at 90 degrees flexion, and FIG. 2C illustrates flexion of 120 degrees or more. In addition to a conventionally placed cam at 101, two additional points of cam action are preferably provided. In particular, a feature at 201 acts to prevent translation from extension into the initiation of the flexion. Feature 201 preferably disengages as conventional cam 101 is engaged. As the knee follows through a range of motion to 90° of flexion, and beyond, cam 101 disengages and feature 202 engages, if necessary, to prevent dislocation of the component.

Figure 2D:
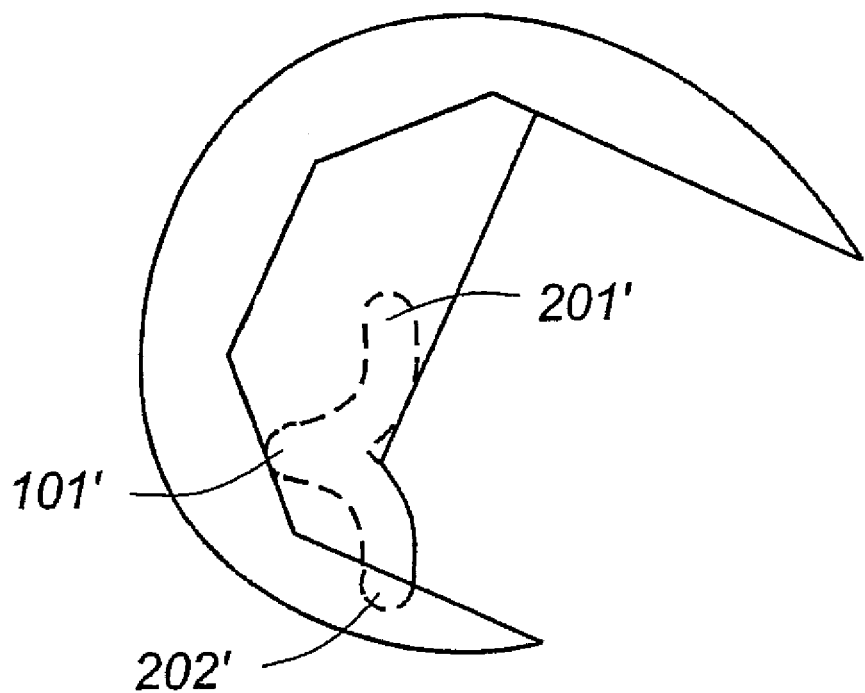
FIG. 2D illustrates the alternative use of interconnected cams with physically separate contact points.
Figure 2E:
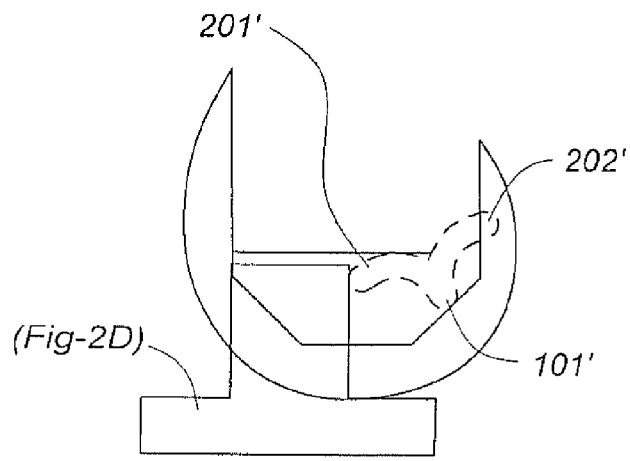
FIG. 2E illustrates the distal femoral component of FIG. 2D and the post configuration of FIG. 6A at full extension.
Figure 2F:
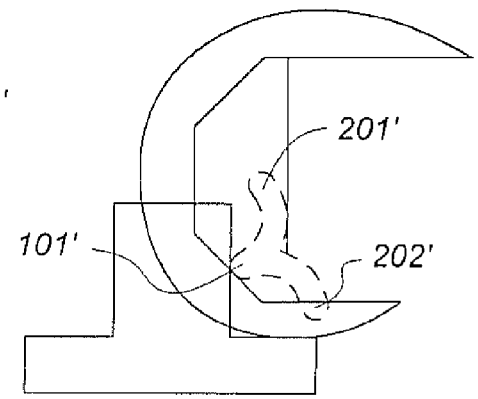
FIG. 2F shows the distal femoral component of FIG. 2D and the post configuration of FIG. 6A at 90 degrees of flexion.
Figure 2G:
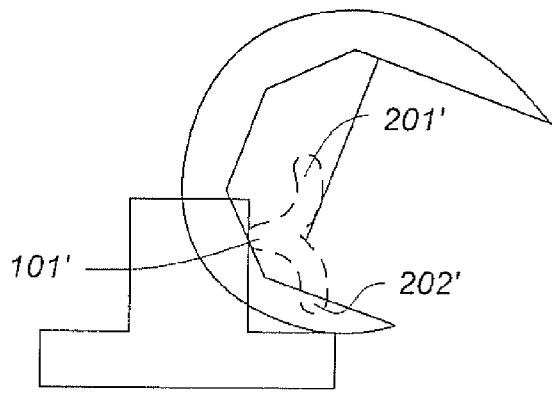
FIG. 2G illustrates the distal femoral component of FIG. 2D and the post configuration of FIG. 6A in flexion beyond 90 degrees.
Figure 2H:
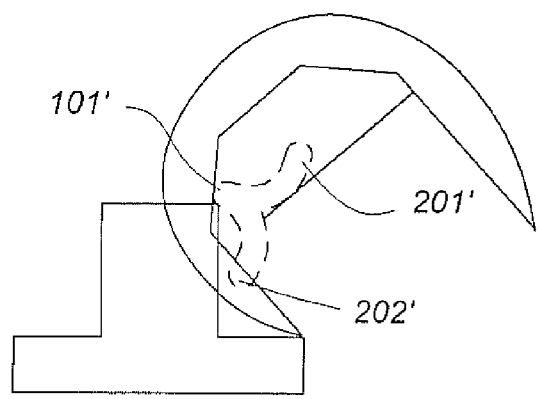
FIG. 2H shows a degree of hyperflexion wherein the extended cam in FIG. 2D first makes contact with the posted or surface of the post.

In FIG. 2B, the cam which is usually present at 101 is engaging the tibial post, cam 201 has disengaged, and cam 202 has not yet engaged but is available for engagement on further flexion. In FIG. 2C, cam 202 is now engaged the post in the presence of additional flexion. Cam 101 can now disengage, cam 201 had disengaged earlier. FIG. 2D illustrates the alternative use of interconnected cams with physically separate contact points.

In FIGS. 2A through 4, the features depicted to provide the various stages of cam/pivoting function are depicted as bars which cross the intercondylar recess or box portion of a cruciate substituting design knee. However, although the terms "cam" or "bar" are used to reference the stages of cam action, it should be understood that the responsible structures may be implemented using any member or combination of elements operative to provide distinct stages of cooperation with the posterior aspect of the superior post. Thus, the members or elements need not be complete or straight across, but may instead be curved, with the post being curved to allows for a rotation, if so desired. The cam structures according to the invention may also be connected to one another forming points of contact as opposed to complete transverse elements. The structure may be provided as part of an open- or closed-type of a box structure, both being familiar to those of skill in the art.

Figure 1A:
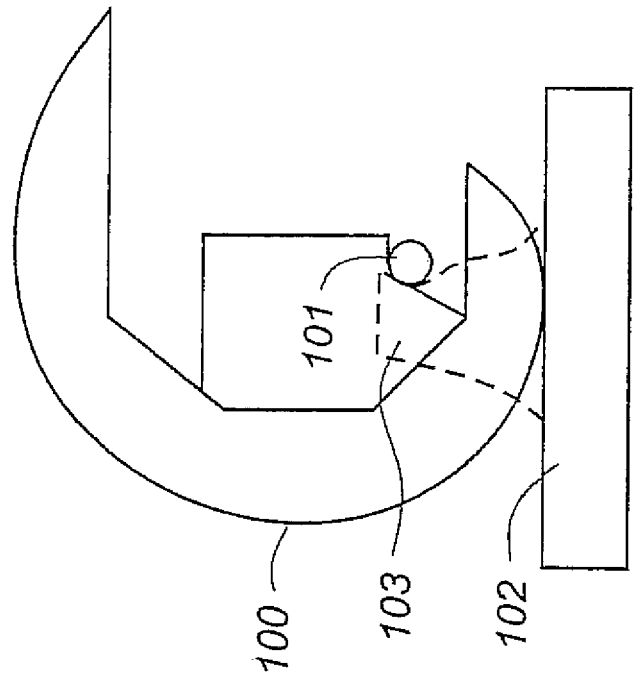
FIG. 1A is a drawing which illustrates a prior-art cam-and-post mechanism in extension.
Figure 1B:
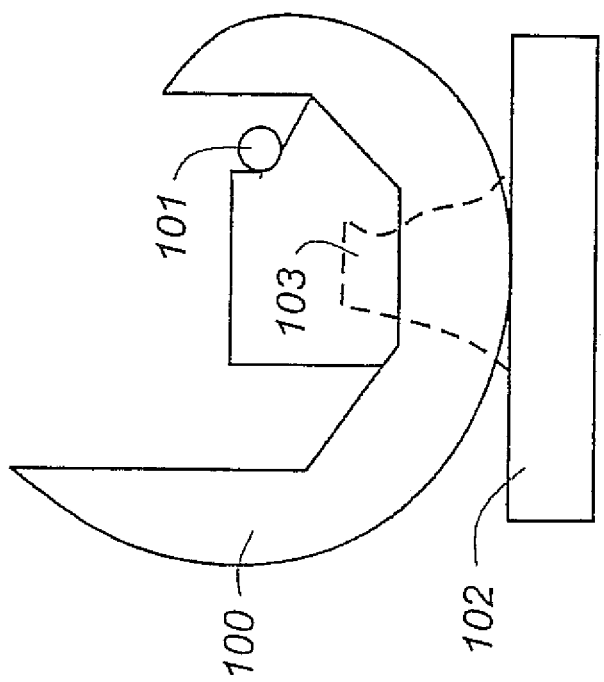
FIG. 1B is a drawing which illustrates the prior-art cam-and-post mechanism of FIG. 1B in flexion.

Whereas FIGS. 1 and 2 represent lateral or side views of a knee through various ranges of motion, FIG. 3 shows an anterior view of a prior-art cruciate substituting knee component at 300 having an open-type box 302 including a single transverse member 301 for illustrative purposes. FIG. 4 shows a knee prosthesis 400 according to the invention, viewed again from the distal-to-proximal perspective, having three distinct points of cam action. In particular, cam 401 is conventionally located, an anterior cam is disposed at 402 in support of a greater range of enhanced flexion, and a more posterior cam at 403 is used primarily to prevent dislocation of the cams over the post, as discussed above.

FIG. 5 is a drawing which shows various cams from a top view looking down. Note that bars of need not be straight across, but may be curved with the post being curved so that it allows for a rotation to occur if desired. The cam structures according to the invention may be individual distinct bars or may be connected to one another forming points of contact as opposed to distinct structures themselves. It should also be noted that the cam structures may be located at different locations from the posterior to the anterior aspect of the knee design, as well as from the distal or proximal, depending upon implant size, patient physiology, desired range of motion, and other requirements. It should further be noted that as opposed to using three separate cams, one could use two cams intended to contact the posted or aspect of the post or for that matter, use more than three if desired.

Figure 6A:
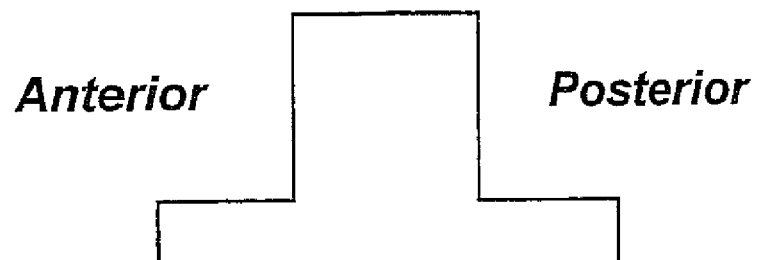
FIGS. 6A through 6E illustrate various alternative post configurations, all of which are applicable to the invention.
Figure 6B:
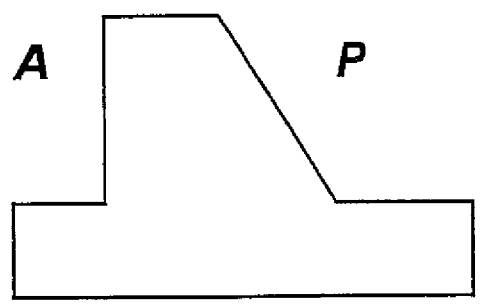
Figure 6C:
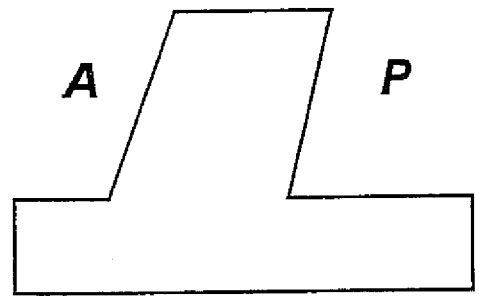
Figure 6D:
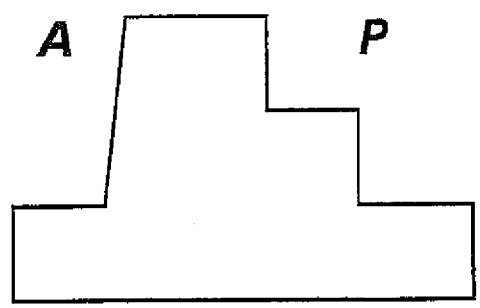
Figure 6E:
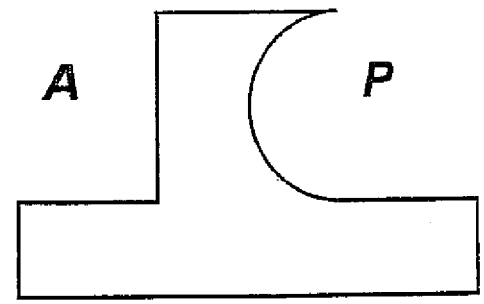

It will also be apparent to one of skill in the art that the posterior aspect of the post may be modified to affect the timing and/or operation of the cam engagement. FIGS. 6A through 6E illustrate various alternative post configurations, all of which are applicable to the invention. As opposed to a substantially straight configuration, as depicted in FIG. 6A, the post may be posteriorly oriented along the posterior aspect, as shown in FIG. 6B. Alternatively, the post may be anteriorly oriented along the posterior aspect, as shown in FIG. 6C. As further alternatives, the post may be stepped, as shown in FIG. 6D, or curved, as shown in FIG. 6E. Also, as opposed to the sharp corners shown, they may be rounded off, and the bars or recesses may be adjusted from the positions shown in FIG. 2 through 5 to achieve a desired operation.

I claim:

1. In a total knee-replacement system including a tibial component having medial and lateral bearing surfaces and a superior post with a posterior surface, and a distal femoral component having medial and lateral condylar protrusions that articulate with the medial and lateral bearing surfaces and an intercondylar region with a central earn that engages with the posterior surface of the superior post, the improvement comprising:
   a distal femoral component having central cam with a convex outer cam action surface area in the intercondylar region that engages the posterior surface of a tibial post before 90 degrees of flexion; and a cam extension providing a separate cam action surface area that makes initial contact with the posterior surface of the post after 90 degrees of flexion to facilitate enhanced knee flexion without dislocation over the tibial post; and wherein the separate cam action surface area of the cam extension faces proximally away from a tibial articulating surface when a knee is in extension.

2. The total knee-replacement system of claim 1, wherein the distal femoral component engages with a tibial component having a superior post with a posterior surface that is substantially flat, curved or slanted.

3. The total knee-replacement system of claim 1, wherein:
a transverse plane is defined as a horizontal plane that divides a human body or any of its parts into upper and lower portions; and
the distal femoral component engages with a tibial component having a superior post that is rounded in the transverse plane to facilitate at least a limited degree of rotation.

4. The total knee-replacement system of claim 1, wherein:
the medial and lateral condylar protrusions of the distal femoral component have a radii of curvature; and
the cam extension has a radius of curvature less than any of the radii of curvature of the medial and lateral condylar protrusions.

5. The total knee replacement system of claim 1, wherein the cam extension projects proximally with the knee in extension.

6. The total knee replacement system of claim 1 wherein a cam action surface of a central cam is still in contact with the posterior surface of a tibial post when the separate cam action surface of the cam extension makes initial contact with the posterior surface of the tibial post.

7. A total knee replacement system, comprising:
a tibial component having medial and lateral bearing surfaces and a tibial post with a posterior surface;
a distal femoral component having an intercondylar region configured to receive the tibial post and medial and lateral condylar surfaces that articulate with the bearing surfaces of the tibial component over a range of motion from extension through flexion; and
a member on the distal femoral component bridging the intercondylar region, the member including:
a central cam having a convex outer surface area that engages with the posterior surface of the tibial post following the onset of flexion, and
a cam extension providing a separate cam action surface area that initially engages with the posterior surface of the tibial post beyond 90 degrees of flexion to minimize dislocation over the tibial post; and
wherein the separate cam action surface area of the cam extension faces proximally away from a tibial articulating surface when a knee is in extension.

8. The total knee-replacement system of claim 7, wherein the posterior surface of the post is substantially flat, curved or slanted.

9. The total knee-replacement system of claim 7, wherein:
a transverse plane is defined as a horizontal plane that divides a human body or any of its parts into upper and lower parts; and
the superior post is rounded in the transverse plane to facilitate at least a limited degree of rotation.

10. The total knee-replacement system of claim 7, wherein:
the medial and lateral condylar protrusions have a radii of curvature; and the cam extension has a radius of curvature substantially less than any of the radii.

11. The total knee replacement system of claim 7 wherein a cam action surface of a central cam is still in contact with the posterior surface of a tibial post when the separate cam action surface of the cam extension makes initial contact with the posterior surface of the tibial post.

12. A knee implant for use in posterior cruciate sacrificing procedures, comprising:
a tibial component having a superior post with a posterior surface;
a femoral component having medial and lateral condylar protrusions which form separated bearing surfaces configured to articulate with the tibial component and an intercondylar femoral cam mechanism;
the cam mechanism including an intercondylar bridging structure with a convex outer surface area which engages with the posterior surface of the superior post;
a cam extension with a separate cam action surface area configured to engage with the posterior surface of the superior post to reduce risk of dislocation;
wherein the cam action surface area of the cam extension engages with the superior post only at flexion greater than 90 degrees; and
wherein the separate cam action surface of the cam extension faces proximally away from a tibial articulating surface when a knee is in extension.

13. The knee implant of claim 12, wherein an anterior surface of the femoral cam mechanism is concave in a transverse plane to facilitate rotation between the femoral and tibial components in the transverse plane.

14. The knee implant of claim 12, wherein the cam extension at least partially bridges an intercondylar region.

15. The knee implant of claim 12, wherein the cam extension projects proximally with the knee in extension.

16. The knee implant system of claim 12 wherein a cam action surface of a central cam is still in contact with the posterior surface of a tibial post when the separate cam action surface of the cam extension makes initial contact with the posterior surface of the tibial post.

17. A total knee replacement system, comprising:
a tibial component having medial and lateral bearing surfaces and a tibial post with a posterior surface;
a distal femoral component having an intercondylar region configured to receive the tibial post and medial and lateral condylar surfaces that articulate with the bearing surfaces of the tibial component over a range of motion from extension through flexion; and
a member on the distal femoral component bridging the intercondylar region, the member including:
a cam with a convex outer surface area that engages with the posterior surface of the tibial post following onset of flexion, and
a cam extension providing a separate cam action surface area that initially engages with the posterior surface of the tibial post beyond 90 degrees of flexion to minimize dislocation over the tibial post, and
wherein the cam action surface area of the cam extension faces proximally away from the tibial articulating surface when a knee is in extension.

18. The total knee replacement system of claim 17 wherein an additional cam extension with a cam action point projects distally toward a tibial articulating surface when the knee is in extension and contacts the posterior surface of the tibial post early after the initiation of flexion to minimize early translation of a femur relative to a tibia.

19. The total knee replacement system of claim 17 wherein the cam is curved in a transverse plane to allow axial rotation.

20. The total knee replacement system of claim 17 wherein a cam action surface of a central cam is still in contact with the posterior surface of a tibial post when the separate cam action surface of the cam extension makes initial contact with the posterior surface of the tibial post.

\* \* \* \* \*